(12) United States Patent
Shrivastava et al.

(10) Patent No.: US 8,524,148 B2
(45) Date of Patent: Sep. 3, 2013

(54) METHOD OF INTEGRATING THERAPEUTIC AGENT INTO A BIOERODIBLE MEDICAL DEVICE

(75) Inventors: Sanjay Shrivastava, Mountain View, CA (US); John Toner, Libertyville, IL (US); Sandra Burke, Libertyville, IL (US); Keith Cromack, Gurnee, IL (US); Peter Tarcha, Lake Villa, IL (US); Donald Verlee, Libertyville, IL (US); Ho-Wah Hui, Libertyville, IL (US)

(73) Assignee: Abbott Laboratories, Abbott Park, IL (US)

(*) Notice: Subject to any disclaimer, the term of this patent is extended or adjusted under 35 U.S.C. 154(b) by 1102 days.

(21) Appl. No.: 11/563,285

(22) Filed: Nov. 27, 2006

(65) Prior Publication Data

US 2007/0189915 A1    Aug. 16, 2007

Related U.S. Application Data

(63) Continuation-in-part of application No. 10/704,114, filed on Nov. 7, 2003, and a continuation-in-part of application No. 10/703,891, filed on Nov. 7, 2003, now abandoned.

(60) Provisional application No. 60/424,574, filed on Nov. 7, 2002, provisional application No. 60/424,575, filed on Nov. 7, 2002, provisional application No. 60/424,576, filed on Nov. 7, 2002, provisional application No. 60/424,577, filed on Nov. 7, 2002, provisional application No. 60/424,607, filed on Nov. 7, 2002.

(51) Int. Cl.
*B22F 3/02* (2006.01)

(52) U.S. Cl.
USPC ............ 419/66; 419/2; 419/5; 419/8; 419/10; 419/32; 419/62; 623/1.42; 623/1.15

(58) Field of Classification Search
USPC ....................................... 419/2, 66
See application file for complete search history.

(56) References Cited

U.S. PATENT DOCUMENTS

| | | | | |
|---|---|---|---|---|
| 4,322,398 A | * | 3/1982 | Reiner et al. ................ | 424/425 |
| 4,877,745 A | | 10/1989 | Hayes et al. | |
| 5,246,530 A | * | 9/1993 | Bugle et al. ................... | 216/56 |
| 5,464,650 A | | 11/1995 | Berg et al. | |

(Continued)

FOREIGN PATENT DOCUMENTS

| | | |
|---|---|---|
| DE | 19940241 | 3/2001 |
| DE | 19940242 | 3/2001 |

(Continued)

OTHER PUBLICATIONS

Marylène Trécant, et al., "Dynamic compaction: a new process to compact therapeutic agent-loaded calcium phosphates," Biomaterials 18 (1997) 141-145.*

(Continued)

*Primary Examiner* — Roy King
*Assistant Examiner* — Christopher Kessler
(74) *Attorney, Agent, or Firm* — Squire Sanders (US) LLP

(57) ABSTRACT

A method of making a medical device which is at least partially bio-erodible and which exhibits controlled elution of therapeutic agent.

2 Claims, 6 Drawing Sheets

(56) References Cited

U.S. PATENT DOCUMENTS

| | | | |
|---|---|---|---|
| 5,591,227 A | 1/1997 | Dinh et al. | |
| 5,605,696 A | 2/1997 | Eury et al. | |
| 5,649,977 A | 7/1997 | Campbell | |
| 5,667,840 A | 9/1997 | Tingey et al. | |
| 5,741,429 A | 4/1998 | Donadio, III et al. | |
| 5,824,048 A | 10/1998 | Tuch | |
| 5,824,049 A | 10/1998 | Ragheb et al. | |
| 5,830,396 A * | 11/1998 | Higgins et al. | 264/109 |
| 5,837,313 A | 11/1998 | Ding et al. | |
| 5,873,904 A | 2/1999 | Ragheb et al. | |
| 5,951,586 A | 9/1999 | Berg et al. | |
| 5,972,027 A * | 10/1999 | Johnson | 623/1.42 |
| 5,980,972 A | 11/1999 | Ding | |
| 6,027,863 A | 2/2000 | Donadio, III | |
| 6,033,434 A | 3/2000 | Borghi | |
| 6,086,942 A | 7/2000 | Carden, Jr. et al. | |
| 6,096,070 A | 8/2000 | Ragheb et al. | |
| 6,107,004 A | 8/2000 | Donadio, III | |
| 6,121,027 A | 9/2000 | Clapper et al. | |
| 6,153,252 A | 11/2000 | Hossainy et al. | |
| 6,187,322 B1 | 2/2001 | Hille et al. | |
| 6,209,621 B1 | 4/2001 | Treacy | |
| 6,231,600 B1 | 5/2001 | Zhong | |
| 6,240,616 B1 | 6/2001 | Yan | |
| 6,251,136 B1 | 6/2001 | Guruwaiya et al. | |
| 6,254,634 B1 | 7/2001 | Anderson et al. | |
| 6,273,913 B1 | 8/2001 | Wright et al. | |
| 6,287,332 B1 | 9/2001 | Bolz et al. | |
| 6,299,604 B1 | 10/2001 | Ragheb et al. | |
| 6,319,277 B1 | 11/2001 | Rudnick et al. | |
| 6,335,029 B1 | 1/2002 | Kamath et al. | |
| 6,358,556 B1 | 3/2002 | Ding et al. | |
| 6,379,379 B1 | 4/2002 | Wang | |
| 6,387,121 B1 | 5/2002 | Alt | |
| 6,395,326 B1 | 5/2002 | Castro et al. | |
| 6,409,716 B1 | 6/2002 | Sahatjian et al. | |
| 6,488,701 B1 * | 12/2002 | Nolting et al. | 623/1.13 |
| 6,506,437 B1 | 1/2003 | Harish et al. | |
| 6,574,851 B1 * | 6/2003 | Mirizzi | 29/527.5 |
| 6,599,516 B1 * | 7/2003 | Knaack | 424/423 |
| 6,616,765 B1 | 9/2003 | Castro et al. | |
| 6,645,547 B1 | 11/2003 | Shekalim et al. | |
| 6,676,987 B2 | 1/2004 | Zhong et al. | |
| 6,713,119 B2 | 3/2004 | Hossainy et al. | |
| 6,743,463 B2 | 6/2004 | Weber et al. | |
| 6,808,536 B2 | 10/2004 | Wright et al. | |
| 7,208,190 B2 | 4/2007 | Verlee | |
| 8,221,495 B2 | 7/2012 | Shrivastava et al. | |
| 2002/0004060 A1 * | 1/2002 | Heublein et al. | 424/422 |
| 2003/0004564 A1 | 1/2003 | Elkins et al. | |
| 2003/0018380 A1 | 1/2003 | Craig et al. | |
| 2003/0068355 A1 | 4/2003 | Shanley et al. | |
| 2003/0083646 A1 | 5/2003 | Sirhan et al. | |
| 2003/0207019 A1 | 11/2003 | Shekalim | |
| 2004/0053953 A1 | 3/2004 | Verlee | |
| 2004/0130584 A1 | 7/2004 | Kobayashi | |
| 2004/0185081 A1 | 9/2004 | Verlee | |
| 2004/0254634 A1 | 12/2004 | Verlee | |
| 2007/0053953 A1 | 3/2007 | Verlee | |
| 2007/0189915 A1 | 8/2007 | Shrivastava | |
| 2007/0191943 A1 | 8/2007 | Verlee | |
| 2008/0020129 A1 | 1/2008 | Verlee et al. | |

FOREIGN PATENT DOCUMENTS

| | | |
|---|---|---|
| EP | 0850651 | 12/1997 |
| WO | WO9800107 | 1/1998 |
| WO | WO9832474 | 7/1998 |
| WO | WO0176525 | 10/2001 |
| WO | WO0191918 | 12/2001 |
| WO | WO 02/069848 | 9/2002 |
| WO | WO 2004/043298 | 5/2004 |
| WO | WO 2004/043299 | 5/2004 |
| WO | WO 2004/043300 | 5/2004 |

OTHER PUBLICATIONS

Cooley et al., "Applications of Ink-Jet Printing Technology to BioMEMS and Microfluidic Systems," Prov. SPIE Conf. on Microfluidics, Oct. 2001.

* cited by examiner

US 8,524,148 B2

METHOD OF INTEGRATING THERAPEUTIC AGENT INTO A BIOERODIBLE MEDICAL DEVICE

CROSS-REFERENCE TO RELATED APPLICATIONS

The present application is a continuation-in-part of U.S. patent application Ser. No. 10/704,114, filed Nov. 7, 2003 and U.S. patent application Ser. No. 10/703,891, filed Nov. 7, 2003, now abandoned, each of which claim the benefit of U.S. Provisional Application Ser. No. 60/424,574, filed Nov. 7, 2002; U.S. Provisional Application Ser. No. 60/424,575, filed Nov. 7, 2002; U.S. Provisional Application Ser. No. 60/424,576, filed Nov. 7, 2002; U.S. Provisional Application Ser. No. 60/424,577, filed Nov. 7, 2002; and U.S. Provisional Application Ser. No. 60/424,607, filed Nov. 7, 2002, each of which are incorporated by reference in their entireties herein.

BACKGROUND OF THE INVENTION

1. Field of the Invention

The invention generally relates to a method of integrating therapeutic agent into a bioerodible implantable medical devices. Particularly, the invention relates to a method of making a drug eluting bioerodible implantable medical device having a controlled elution.

2. Description of Related Art

Percutaneous transluminal coronary angioplasty (PTCA) is a procedure for treating heart disease. This procedure generally entails introducing a catheter assembly into the cardiovascular system of a patient via the brachial or femoral artery, and advancing the catheter assembly through the coronary vasculature until a balloon portion thereon is positioned across an occlusive lesion. Once in position across the lesion, the balloon is inflated to a predetermined size to radially compress against the atherosclerotic plaque of the lesion to remodel the vessel wall. Subsequently, the balloon is deflated to allow the catheter assembly to be withdrawn from the vasculature.

While PCTA is widely used, it suffers from two unique problems. First, the blood vessel may suffer acute occlusion immediately after or within the initial hours after the dilation procedure. Second, the re-narrowing of an artery or other blood vessel after an initially successful angioplasty sometimes results. This blood vessel re-narrowing is commonly referred to as "restenosis," which typically occurs within the first six months after angioplasty. Restenosis is believed to be due to, among other things, the proliferation and migration of cellular components from the arterial wall, as well as through geometric changes in the arterial wall referred to as "remodeling."

To reduce occlusion of the artery or blood vessel, and the development of thrombosis and/or restenosis, an expandable stent is implanted in the lumen to maintain the vascular patency. Typically, expandable stents are formed from metal, including for example, 316 stainless steel, MP35N alloy and superelastic nickel-titanium. Additionally, it has become common to coat the implantable metal stent with particular drugs to prevent restenosis. One drawback of metal stent implants is stent occlusion, which may occur due to collapse of the stent. To overcome such disadvantages, bioerodible or bioabsorbable stents have been proposed, for example, in U.S. Pat. No. 6,287,332 to Bolz and U.S. Patent Publication No. 2004/0138738 to Stinson, the entire contents of each of which are incorporated herein by reference. However, there remains a need for an improved bioerodible medical device, including bioerodible stents.

SUMMARY OF THE INVENTION

The purpose and advantages of the embodiments of the invention will be set forth in and will be apparent from the description that follows, as well as will be learned by practice of the invention. Additional advantages of the invention will be realized and attained by the methods and devices particularly pointed out in the written description and claims hereof, as well as from the appended drawings.

To achieve these and other advantages and in accordance with the purpose of the invention, as embodied and broadly described, the invention includes a medical device for implanting into the lumen of a vessel or an organ with a lumen. For example and not limitation, the implantable medical device can be intended for implantation in an artery or a tear duct. The medical device is, for example and not limitation, a stent, graft or stent-graft structure or other tubular member adapted for delivery into a anatomical lumen. The implantable medical device has a body comprising bioerodible material and at least one therapeutic agent associated with the bioerodible material. The bioerodible material can be a metal, metal alloy, polymer or any combination thereof. In a further aspect of the invention, the bioerodible material includes a first bioerodible material and a second bioerodible material. In this manner, the first bioerodible material can have a rate of elution that is different than the rate of elution of the second bioerodible material.

In accordance with an aspect of the invention, the implantable medical device is partially bioerodible. In this regard, the body includes non-bioerodible material in addition to the bioerodible material. For example and not limitation, the medical device can include a first portion or layer comprising non-bioerodible material and a second portion or a layer comprising bioerodible material. The non-bioerodible material can be any suitable metal, metal alloy, ceramic or polymer material that does not erode in the anatomical body.

In accordance with the invention, at least one therapeutic agent is associated with the medical device. In this regard, the therapeutic agent can be integrated with the bioerodible material, the non-bioerodible material, if present, or both. In this manner, the medical device can include a body comprising a plurality of pores defined along a surface thereof and at least one therapeutic agent can be disposed in at least some of the pores. In accordance with a further aspect of the invention, a controlled rate of elution of the therapeutic agent(s) is achieved by the configuration and dimension of the plurality of pores including pore size, pore size distribution and/or pore arrangement on the medical device. For example, each of the plurality of pores can have a uniform size or alternatively, the size of at least some of the plurality of pores can vary. Further, the different sized pores can be arranged on the medical device in a predetermined manner to alter the elution rate profile of the device.

In further accordance with the invention, a first therapeutic agent can be disposed in some of the plurality of pores and a second therapeutic agent can be disposed in other pores of the plurality. Alternatively, at least some of the plurality of pores can include a combination of first and second therapeutic agents. As yet another alternative, at least some of the plurality of pores can be at least partially filled with a polymer material. In this regard, the polymer material can be free of therapeutic agent or can be mixed with therapeutic agent. Further, the at least one therapeutic agent can be present in a coating applied to the bioerodible material, for example, a polymer coating including therapeutic agent.

In another aspect of the invention, if more than one therapeutic agent is used, the first therapeutic agent can have a release rate different than the release rate of the second therapeutic agent, if desired. Further, a third therapeutic agent can have a different release rate than at least one of the first or second therapeutic agents.

Additionally, at least one therapeutic agent can be associated with the non-bioerodible material, if present, in the same manner as that of the bioerodible material. In other words, at least one therapeutic agent can be integral with the non-bioerodible material, coated on a surface of the non-bioerodible material or disposed in pores formed in the non-bioerodible material.

In accordance with the invention, at least one therapeutic agent can be selected from but not limited to anti-proliferative, anti-inflammatory, antineoplastic, antiplatelet, anti-coagulant, anti-fibrin, antithrombonic, antimitotic, antibiotic, antiallergic and antioxidant compounds. Thus, the therapeutic agent may be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, a retroviral vector, an anti-proliferative agent including rapamycin (sirolimus), 40-O-(2-hydroxyethyl)rapamycin (everolimus), 40-O-(3-hydroxypropyl)rapamycin, 40-O-(2-hydroxyethyoxy)ethylrapamycin, 40-O-tetrazolylrapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anticoagulant, an antifibrin, an antithrombins including sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor including Angiomax ä, a calcium channel blocker including nifedipine, colchicine, a fibroblast growth factor (FGF) antagonist, fish oil (omega 3-fatty acid), a histamine antagonist, lovastatin, a monoclonal antibodie, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement including vitamins, an anti-inflammatory agent including aspirin, tacrolimus, dexamethasone and clobetasol, a cytostatic substance including angiopeptin, an angiotensin converting enzyme inhibitor including captopril, cilazapril or lisinopril, an antiallergic agent including permirolast potassium, alpha-interferon, bioactive RGD, and genetically engineered epithelial cells. Other therapeutic agents which are currently available or that may be developed in the future for use with implantable medical devices may likewise be used and all are within the scope of this invention.

When desired or necessary, the therapeutic agent can include or be mixed with a polymer to carry, load, or control the release of the therapeutic agent. The term "polymer" is intended to include but not be limited to a product of a polymerization reaction inclusive of homopolymers, copolymers, terpolymers, whether natural or synthetic, including random, alternating, block, graft, branched, cross-linked, blends, compositions of blends and variations thereof. The polymer may be in true solution, saturated, or suspended as particles or supersaturated in the therapeutic agent. The polymer can be biocompatible or bioerodible. One non-limiting example of a suitable polymer is phosphorylcholine.

In accordance with yet a further aspect of the invention, an implantable medical device is provided wherein at least one therapeutic agent is mixed with a solvent. The solvent can be, for example but not limitation, an alcohol including ethanol or isobutanol.

Embodiments of the invention also encompasses, for any of the embodiments disclosed, the application of a rate-controlling topcoat over the therapeutic agent for controlling or sustaining the release of the at least one therapeutic agent. For example and not limitation, the topcoat can comprise a polymer.

In accordance with another aspect of the invention, a method of making an implantable medical device comprising a body including bioerodible material and at least one therapeutic agent associated with the body. The association of the therapeutic agent with the body of the medical device can be achieved in a variety of techniques. In this manner, the therapeutic agent can be released from the medical device as the bioerodible material elutes into the surrounding biological environment. For example and not limitation, the therapeutic agent can form an integral part of the microstructure of the bioerodible material. The integrating step can be performed by for example layered deposition, creating a porous structure and disposing the therapeutic agent in the porous structure, combining the therapeutic agent in the bioerodible powder and depositing it through powder metallurgy techniques.

In a further aspect of the invention, the method can further include the step of mixing at least one therapeutic agent with a polymer to control the release of the therapeutic agent. Additionally, the method can include applying rate controlling topcoat along the body of the medical device.

DETAILED DESCRIPTION OF THE EMBODIMENT

Reference will now be made in detail to the present embodiments of the invention. The method and corresponding steps of the invention will be described in conjunction with the detailed description of the medical device.

In accordance with one aspect of the embodiments of the invention, an implantable medical device is provided for delivery of at least one therapeutic agent within a lumin or to a tissue. Particularly, the present invention is suited for providing an implantable medical device having a body including at least a portion of bioerodible material. Generally, the "bioerodible material" means a material that undergoes structural or chemical changes such that the remaining structure is less than the original structure, when placed in a human or animal body.

As used herein, the term "implantable medical device" refers broadly to any device suitable for implantation. For purposes of illustration and not limitation, the implantable medical device can be a stent, graft, stent-graft, filter, occlusive device and the like. In one embodiment, the implantable medical device is a stent. The stent can be deployed by mechanical means including but not limited to a balloon expanding stent. Alternatively, the stent can be deployed by self actuating means, including a self-expanding stent. The implantable medical device is not intended to be limited to cardiovascular applications. For example and not limitation, other applications are also intended to be in the scope of the invention including spinal or other orthopedic implants, neurovascular or gastrointestinal implants and the like.

Figure 1:
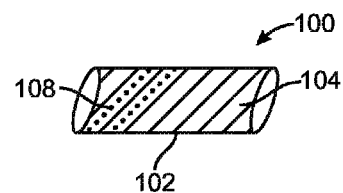
FIG. 1 is a schematic representation of one embodiment of the invention.

An exemplary embodiment of the implantable medical device in accordance with the invention is shown schematically in FIG. 1. As shown in FIG. 1, the implantable medical device 100 generally comprises body 102 comprising bioerodible material 104 and at least one therapeutic agent 108 associated with the bioerodible material. In this manner, the at least one therapeutic agent is exposed and released to the biological environment during elution or decomposition of the bioerodible material.

Specifically, and in accordance with the embodiments of the invention, the bioerodible material herein is a metal, metal alloy, polymer or a combination thereof that decomposes in the biological environment. For example and not limitation, suitable bioerodible materials include magnesium, zinc or silicon, lithium, zinc-titanium, magnesium-lithium, polylactic acid, polyglycolic acid or derivatives thereof, and any combination thereof. Magnesium, PGA-PLA combinations or derivatives and hydroxyapatitie are some of the preferred bioerodible materials.

Figure 2:
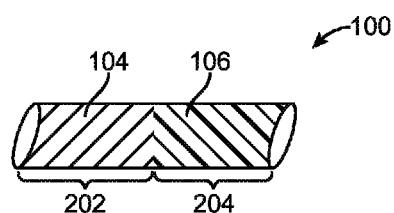
FIG. 2 is a schematic representation of another embodiment of the invention.
Figure 3:
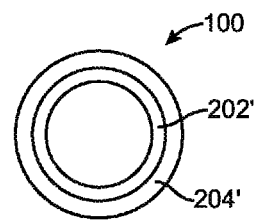
FIG. 3 is a schematic representation of a cross section view of an embodiment of the invention.

The body of the medical device can be entirely composed of bioerodible material, as shown in FIG. 1 or can further include non-bioerodible material 106 as depicted in FIG. 2. In this regard, the medical implant comprises a first portion 202 comprising bioerodible material and a second portion 204 comprising non-bioerodible material. For example and not limitation, the first portion can correspond to a first predetermined length of the medical device and the second portion can correspond to a second predetermined length of the medical device. Alternatively, as embodied herein and depicted in FIG. 3, the first portion can correspond to an inner layer, inner surface or both of the medical device and the second portion can correspond to an outer layer, outer surface or both of the medical device.

For purposes of illustration and not limitation, the non-bioerodible material can be composed any suitable material including, but not limited to, 316 L stainless steel, MP35N®, MP20N®, Elgiloy®, nickel-titanium alloy, platinum-iridium alloy, cobalt-chromium alloy, gold, tantalum alloy, titanium alloy, polymer, ceramic, tissue, or combinations thereof.

Figure 4:
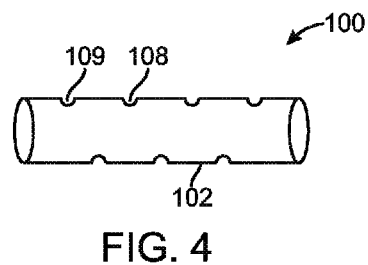
FIG. 4 is a schematic representation of another embodiment of the invention.
Figure 7:
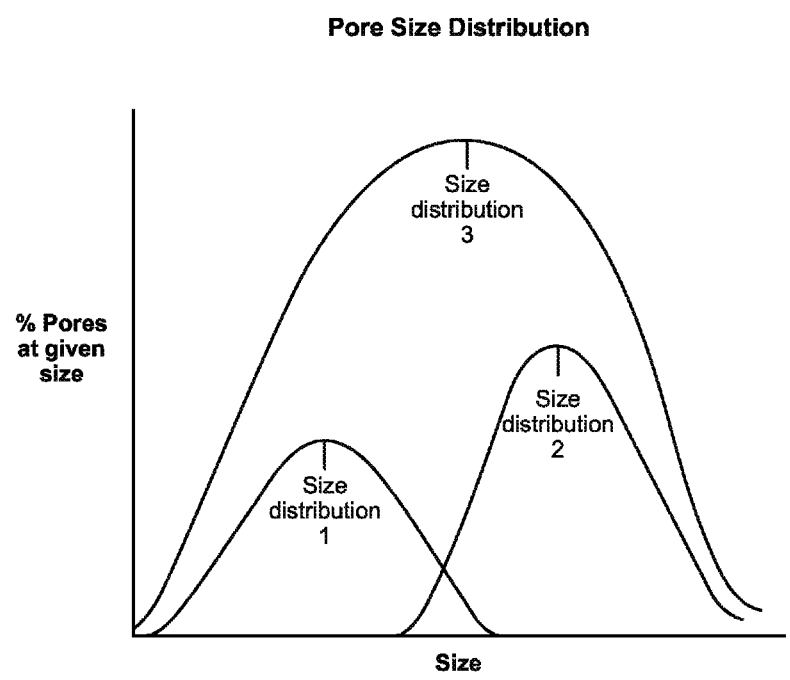
FIG. 7 is a graph of the pore size distribution in accordance with the invention.

In some embodiments, the body of the medical device can include a plurality of pores 109 formed therein, as depicted in FIG. 4. The plurality of pores can be disposed along the entire surface of the medical device or can be disposed only along a portion thereof. Further, the plurality of pores can be disposed along an outer surface of the body of the medical device and/or disposed along an inner surface of the body. In one embodiment, each of the plurality of pores has a uniform size. In another embodiment, some of the plurality of pores have a size that varies or is different than other pores of the plurality. In this manner, the pores will include a pore size distribution, as depicted in FIG. 7. In one embodiment, as depicted in FIG. 7, the plurality of pores include first, second and third pore size distributions. Each pore size distribution includes pores having a particular size range. Each of the first, second, and third size distributions can include pores having a uniform size as depicted by the overlapping sections of each of the size distributions, but the mean pore size distribution for each of the first, second and third pore size distributions is varied. In this manner, a controlled elution profile can be achieved.

The plurality of pores can be sized or spaced from each other to correspond to a predetermined dosage or concentration of therapeutic agent delivered therefrom, if desired. For example but not limitation, the pores 109 can be defined by removing the material from the body of the medical device, for example by leaching, chemical etching, ablation techniques, or any other technique as known in the art.

Figure 8A:
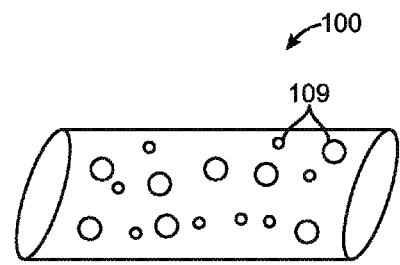
FIGS. 8A to 8C are schematic representations of embodiments of the invention.
Figure 8B:
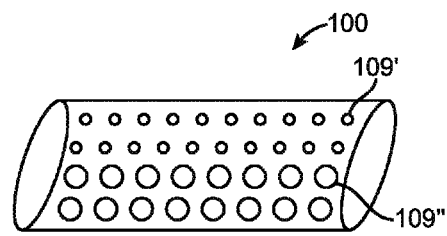
Figure 8C:
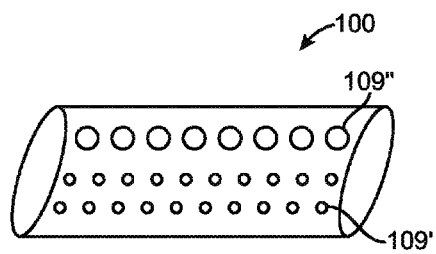

In further accordance with the invention, the plurality of pores 109 including pores having varied sizes are arranged along the medical device in a predetermined arrangement or pattern. In this manner, a controlled elution profile can be achieved. For example and not limitation, the pores can be arranged randomly along the surface of the medical device, as depicted in 8A or alternatively the pores can be arranged in a pattern including a layered arrangement along a portion of the medical device. In a layered arrangement, the pores 109' having a smaller size or smaller size distribution can be arranged on the mural side of the medical device, as depicted in FIG. 8B. Alternatively, the pores 109" having a larger size or larger size distribution can be arranged on the mural size of the medical device, as depicted in FIG. 8C. Thus, the medical device can include a first section having pores having a first size distribution and a second section having pores having a second size distribution.

In accordance with the invention, at least one therapeutic agent 108 is associated with the bioerodible material. It should be noted that at least one therapeutic agent can also be associated with the non-bioerodible material, when present. In either regard, and in accordance with the present invention, at least one therapeutic agent can be disposed in the plurality of pores defined in the body of the medical device. Alternatively, the at least one therapeutic agent can be integrated into the body of the medical device. In this manner, the body includes a microstructure and at least one therapeutic agent is integrated into the microstructure of the body by a various means. For example and not limitation, the therapeutic agent can be integrated into the body by layered deposition, combining the therapeutic agent in metal powder and depositing the mixture on a mandrel through powder metallurgy techniques to form a medical device including a stent. The term "powder metallurgy" refers to creating a shaped device by compressing and fusing metallic powders together. In accordance with the invention, powder metallurgy techniques such as hot pressing and hot isostatic pressing processes can be employed to make the medical device of the invention. Further, conventional coating techniques can be utilized to coat at least one therapeutic agent onto the body of the medical device, including spraying or dipping, for example.

Figure 9:
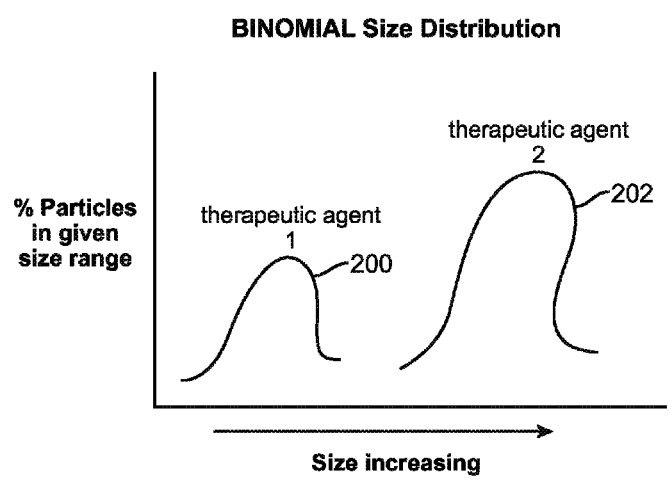
FIG. 9 is a graph of a binomial pore size distribution in accordance with the invention.

In accordance with a further aspect of the invention, the at least one therapeutic agent includes a first therapeutic agent and a second therapeutic agent. The first and second therapeutic agents can be different agents. Further, when desired, the first therapeutic agent can be configured to have a release rate different than the second therapeutic agent or can be released at different time points than the first one, as will be discussed below. For example, the first therapeutic agent can be disposed in the first portion of the medical device and the second therapeutic agent can be disposed in the second portion of the medical device. Additionally or alternatively, if the medical device includes a plurality of pores, some of the plurality of pores can include the first therapeutic agent and the other plurality of pores can include the second therapeutic agent. The first 200 and second 202 therapeutic agents can have a binomial size distribution, as shown in FIG. 9.

The arrangement and size distribution of the plurality of pores impregnated or filled with at least one therapeutic agent achieves a predetermined therapeutic agent elution profile. In this manner, for example, at least one therapeutic agent is distributed homogenously throughout or along a medical device, including a stent, or example. The distribution of therapeutic agent in conjunction with the selected pore size arrangement as depicted in FIGS. 8A to 8C, achieve a varied elution of therapeutic agent. For example, as shown in FIG. 8B, a first therapeutic agent contained in pores having a smaller size distribution on the mural side of the stent will elute before the second therapeutic agent contained in larger size pores of the medical device, as the pores function as elution or diffusion channels. Alternatively, the second therapeutic agent contained in pores having a larger size distribution on the mural side of the stent will elute prior to the first therapeutic agent contained in the remaining pores of the stent. Thus, by controlling the pore size in conjunction with the pore arrangement on the medical device, a desired elution profile can be achieved by the invention.

Figure 10:
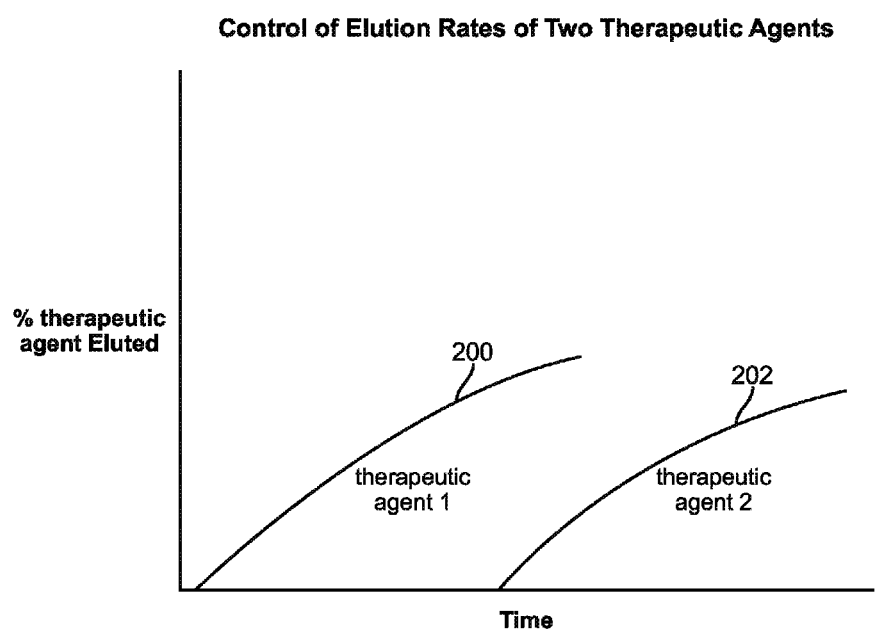
FIG. 10 is a graph depicting controlled elution rates of two therapeutic agents in accordance with the invention.

In another embodiment, as depicted in FIG. 10, first 200 and second 202 therapeutic agents are arranged in a layered structure, which further contributes to the controlled elution rates of the therapeutic agents.

The pores formed in the medical device can have a variety of shapes. For example and not limitation, the pores can be configured to have be generally spherical, cubic, tetrahedral, acicular and other shapes, if desired. The plurality of pores can include an arrangement of pores having a plurality of different shapes. In this manner, the predetermined shapes of the pores can be chosen to correspond to the shape of the particular particles of the therapeutic agents. By predetermined shapes of pores and corresponding the shape of the pores with a particular therapeutic agent, the elution of the therapeutic agent can be controlled.

The pore size, pore shapes and pore size arrangements can be controlled through varying the parameters of powder metallurgic processes. Such parameters include pressure, temperature, direction of pressure (e.g., bidirectional or isostatic), types of binders employed.

For example and not limitation, at least one therapeutic agent can include anti-proliferative, anti-inflammatory, anti-neoplastic, antiplatelet, anti-coagulant, anti-fibrin, anti-thrombonic, antimitotic, antibiotic, antiallergic and antioxidant compounds. Thus, the therapeutic agent may be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, a retroviral vector, an anti-proliferative agent including rapamycin (sirolimus), 40-O-(2-hydroxyethyl)rapamycin (everolimus), 40-O-(3-hydroxypropyl)rapamycin, 40-O-(2-hydroxyethyoxy)ethylrapamycin, 40-O-tetrazolylrapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anticoagulant, an antifibrin, an antithrombins including sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor including Angiomax ä, a calcium channel blocker including nifedipine, colchicine, a fibroblast growth factor (FGF) antagonist, fish oil (omega 3-fatty acid), a histamine antagonist, lovastatin, a monoclonal antibodie, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement including vitamins, an anti-inflammatory agent including aspirin, tacrolimus, dexamethasone and clobetasol, a cytostatic substance including angiopeptin, an angiotensin converting enzyme inhibitor including captopril, cilazapril or lisinopril, an antiallergic agent including permirolast potassium, alpha-interferon, bioactive RGD, and genetically engineered epithelial cells. Other therapeutic agents which are currently available or that may be developed in the future for use with implantable medical devices may likewise be used and all are within the scope of this invention.

For example and limitation, the therapeutic agents effective in preventing restenosis, including those classified into the categories of anti-proliferative agents, anti-platelet agents, anti-inflammatory agents, anti-thrombotic agents, and thrombolytic agents can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, including, for example, daunorubicin, daunomycin, and plicamycin. Other sub-classes of anti-mitotic agents include anti-mitotic alkylating agents, including, for example, tauromustine, bofumustine, and fotemustine, and anti-mitotic metabolites, including, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

An example of an anti-mitotic agent includes, but is not limited to, paclitaxel. As used herein, paclitaxel includes the alkaloid itself and naturally occurring forms and derivatives thereof, as well as synthetic and semi-synthetic forms thereof.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, including, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIbIIIa or αvβ3, antibodies that block binding to gpIIaIIIb or αvβ3, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

As discussed above, at least one therapeutic agent can be an anti-inflammatory agents. Non-limiting examples of anti-inflammatory agents include prednisone, dexamethasone, hydrocortisone, estradiol, triamcinolone, mometasone, fluticasone, clobetasol, and non-steroidal anti-inflammatories, including, for example, acetaminophen, ibuprofen, naproxen, adalimumab and sulindac. The arachidonate metabolite prostacyclin or prostacyclin analogs is an example of a vasoactive antiproliferative. Other examples of these agents include those that block cytokine activity or inhibit binding of cytokines or chemokines to the cognate receptors to inhibit pro-inflammatory signals transduced by the cytokines or the chemokines. Representative examples of these agents include, but are not limited to, anti-IL 1, anti-IL2, anti-IL3, anti-IL4, anti-IL8, anti-IL15, anti-IL18, anti-MCP1, anti-CCR2, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, including, for example, heparin, heparin sulfate, low molecular weight heparins, including, for example, the compound having the trademark Clivarin®, and synthetic oligosaccharides, including, for example, the compound having the trademark Arixtra®. Also included are direct thrombin inhibitors, including, for example, melagatran, ximelagatran, argatroban, inogatran, and peptidomimetics of binding site of the Phe-Pro-Arg fibrinogen substrate for thrombin. Another class of anti-thrombotic agents that can be delivered are factor VII/VIIa inhibitors, including, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Other therapeutic agents include cytotoxic drugs, including, for example, apoptosis inducers, including TGF, and topoisomerase inhibitors, including, 10-hydroxycamptothecin, irinotecan, and doxorubicin. Other therapeutic agents include drugs that inhibit cell de-differentiation and cytostatic drugs. The at least one therapeutic agent can also include anti-lipaedemic agents, including fenofibrate, matrix metalloproteinase inhibitors, including, for example, batimistat, antagonists of the endothelin-A receptor, including, for example, darusentan, and antagonists of the αvβ3 integrin receptor.

In accordance with another embodiment of the invention, the at least one therapeutic agent can be mixed with a polymer to carry or allow controlled release of the therapeutic agent. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the beneficial agent. The polymer can be biocompatible, or biodegradable.

For purpose of illustration and not limitation, the polymeric material include phosphorylcholine linked macromolecules, including a macromolecule containing pendant phosphorylcholine groups including poly($MPC_w$:$LMA_x$:$HPMA_y$:$TSMA_z$), where MPC is 2-methacryoyloxyethylphosphorylcholine, LMA is lauryl methacrylate, HPMA is hydroxypropyl methacrylate and TSMA is trimethoxysilylpropyl methacrylate, polycaprolactone, poly-D,L-lactic acid, poly-L-lactic acid, poly(lactide-co-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, Parylene®, Parylast®, polyurethane including polycarbonate urethanes, polyethylene, polyethylene terapthalate, ethylene vinyl acetate, ethylene vinyl alcohol, silicone including polysiloxanes and substituted polysiloxanes, polyethylene oxide, polybutylene terepthalate-co-PEG, PCL-co-PEG, PLA-co-PEG, polyacrylates, polyvinyl pyrrolidone, polyacrylamide, and combinations thereof. Non-limiting examples of other suitable polymers include thermoplastic elastomers in general, polyolefin elastomers, EPDM rubbers and polyamide elastomers, and biostable plastic material including acrylic polymers, and its derivatives, nylon, polyesters and epoxies.

In further accordance with the present invention, the at least therapeutic agent can be dissolved in a solvent. The solvent can be any single solvent or a combination of solvents. For purpose of illustration and not limitation, examples of suitable solvents include water, aliphatic hydrocarbons, aromatic hydrocarbons, alcohols, ketones, dimethyl sulfoxide, tetrahydrofuran, dihydrofuran, dimethylacetamide, acetates, and combinations thereof.

In another aspect of the invention, the medical device includes a topcoat, including a polymer layer. The topcoat may be added by applying a coating layer over the body of the medical device. In this manner, the topcoat can function to control the rate of release of the therapeutic agent from the medical device. In this regard, the thickness of the topcoat layer is selected to provide a desired rate of release of therapeutic agent.

In another aspect of the invention, a method is provided for making an implantable medical device. In one embodiment, the method includes combining at least one therapeutic agent and bioerodible material in powder form, forming a shaped medical device from the therapeutic agent and bioerodible powder mixture, and binding the mixture to form the medical device. The binding step is achieved for example by sintering techniques. In this manner, at least one therapeutic agent is integrated in the body of a medical device.

Figure 5:
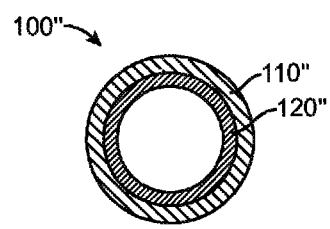
FIG. 5 is a schematic representation of another embodiment of the invention.
Figure 6:
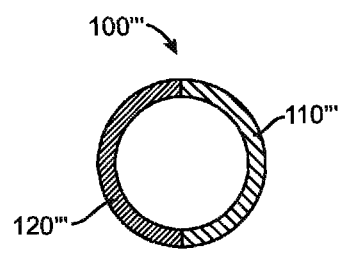
FIG. 6 is a schematic representation of another embodiment of the invention

The bioerodible powder can include bioerodible materials, including but not limited to metal, metal alloy, polymer, or a combination thereof. Further, the method can further include the step of mixing a non-bioerodible powder to the mixture. In this manner, a composite medical device is formed including bioerodible material, non-bioerodible material and at least one therapeutic agent. In one preferred embodiment, the body of the medical device has a functionality gradient material in a radial direction. For example and not limitation, the medical device having a functionality gradient in a radial direction includes a first material disposed adjacent in the radial direction from a second material. As a further illustration when the medical device is a stent 100", as depicted in FIG. 5, the first material 110" is exposed to lumen wall and the second material 120" is disposed to the abluminal. Alternatively, the medical device can have a functionality gradient in a circumferential direction, as shown in FIG. 6. In this manner, the first material 110" is adjacent in a circumferential direction to the second material 120". As further illustration, when the medical device is a stent, the strut can be composed of the first material and the second material in the disposed adjacent each other in the circumferential direction.

In one aspect of the invention, the method further includes combining a non-biodegradable material with the at least one therapeutic agent and/or the biodegradable powder. In this regard, the non-biodegradable material can be in the form of a powder. The non-biodegradable material can be a metal, metal alloy, ceramic or polymer material or any combination thereof. In this manner, a composite medical device is prepared comprising biodegradable material, non-biodegradable material and at least one therapeutic agent.

In a further aspect of the invention, the method can further include applying a topcoat to the formed medical device, as discussed above. The topcoat of the invention can include a polymer or combination of polymers, a therapeutic agent, solvent, or any combination thereof.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents

What is claimed is:

1. A method of making an implantable medical device comprising:
  combining at least one therapeutic agent with a bioerodible material in powder form, wherein the-combining step includes mixing the at least one therapeutic agent with the bioerodible material to define a mixture,
  wherein the mixture is deposited on a mandrel; and
  forming a shaped medical device from the mixture by compressing and fusing the powder of the mixture together, wherein the at least one therapeutic agent is an integral part of a microstructure of the bioerodible material of the device.

2. A method of making a stent comprising:
  providing a bioerodible material in powder form and an anti-proliferative therapeutic agent;
  mixing the bioerodible material and the anti-proliferative therapeutic agent to form a mixture; and
  forming a stent body from the mixture, wherein the forming comprises layered deposition of the mixture on a mandrel,
  wherein the stent body comprises the anti-proliferative therapeutic agent associated with the bioerodible material.

* * * * *

UNITED STATES PATENT AND TRADEMARK OFFICE
CERTIFICATE OF CORRECTION

PATENT NO.        : 8,524,148 B2
APPLICATION NO. : 11/563285
DATED             : September 3, 2013
INVENTOR(S)       : Shrivastava et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1227 days.

Signed and Sealed this
Twenty-third Day of May, 2017

Michelle K. Lee
*Director of the United States Patent and Trademark Office*